(12) United States Patent
Jager

(10) Patent No.: US 7,632,506 B2
(45) Date of Patent: Dec. 15, 2009

(54) IDENTIFICATION OF NEW NY-ESO-1 EPITOPES RECOGNIZED BY CD4+ T-CELLS

(75) Inventor: Elke Jager, Frankfurt am Main (DE)

(73) Assignee: Ludwig Institute for Cancer Research, New York, NY (US)

( * ) Notice: Subject to any disclaimer, the term of this patent is extended or adjusted under 35 U.S.C. 154(b) by 365 days.

(21) Appl. No.: 11/219,610

(22) Filed: Sep. 2, 2005

(65) Prior Publication Data

US 2006/0172937 A1    Aug. 3, 2006

(51) Int. Cl.
*A61K 39/00* (2006.01)

(52) U.S. Cl. .................................. 424/184.1; 530/300

(58) Field of Classification Search ....................... None
See application file for complete search history.

(56) References Cited

U.S. PATENT DOCUMENTS 6,251,603 B1 * 6/2001 Jager et al. .................... 435/6
6,417,165 B1 * 7/2002 Valmori et al. ................ 514/15
6,548,064 B1 * 4/2003 Tureci et al. .............. 424/184.1
6,723,832 B1 * 4/2004 Knuth et al. ................ 530/324
6,800,730 B1 * 10/2004 Tureci et al. ................ 530/350
7,041,502 B2 * 5/2006 Bilsborough et al. ...... 435/372.3
7,115,729 B2 * 10/2006 Knuth et al. ............... 536/23.5
7,385,044 B2 * 6/2008 Tureci et al. ............... 536/23.1

FOREIGN PATENT DOCUMENTS

WO    WO-0155393    *  8/2001
WO    WO-03068800   *  8/2003

* cited by examiner

*Primary Examiner*—Misook Yu
(74) *Attorney, Agent, or Firm*—Fulbright & Jaworski LLP

(57) ABSTRACT

The invention relates to peptides which bind to MHC molecules of either Class I or Class II, and their use. The peptides consist of amino acid sequences found in the NY-ESO-1 molecule.

11 Claims, 7 Drawing Sheets

| | |
|---|---|
| 41-60 | GGRGPRGAGAARASGPGGGA |
| 43-60 | RGPRGAGAARASGPGGGA |
| 49-66 | GAARASGPGGGAPRGPHG |
| 51-70 | ARASGPGGGAPRGPHGGAAS |
| 55-72 | GPGGGAPRGPHGGAASGL |
| 61-78 | PRGPHGGAASGLNGCCRC |
| 61-80 | PRGPHGGAASGLNGCCRCGA |
| 67-84 | GAASGLNGCCRCGARGPE |
| 71-90 | GLNGCCRCGARGPESRLLEF | p49-72 GAARASGPGGGAPRGPHGGAASGL
NW2337-CD4-1 reactive fragment p55-80 GPGGGAPRGPHGGAASGLNGCCRCGA
NW2337-CD4-10 reactive fragment p55-66 GPGGGAPRGPHG core NW2337-CD4-1 peptide
p61-72 PRGPHGGAASGL core NW2337-CD4-10 peptide

SEQUENCE LISTING

<160> NUMBER OF SEQ ID NOS: 1

<210> SEQ ID NO 1
<211> LENGTH: 180
<212> TYPE: PRT
<213> ORGANISM: H. sapiens

<400> SEQUENCE: 1

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Ala Pro Arg Gly Ala
        35                  40                  45

Gly Ala Ala Arg Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Pro
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

IDENTIFICATION OF NEW NY-ESO-1 EPITOPES RECOGNIZED BY CD4+ T-CELLS

FIELD OF THE INVENTION

This invention relates to the immunogenic protein known as NY-ESO-1. Previously, immunogenic peptides consisting of amino acids in the sequence of NY-ESO-1 were identified. More have now been found.

BACKGROUND AND PRIOR ART

NY-ESO-1 is one of the most immunogenic cancer testis antigens, able to induce strong humoral (antibody) and cellular (T cell) immune responses in patients with NY-ESO-1 expressing cancers either through natural or spontaneous induction by the patients tumor or following specific vaccinination using define peptides epitopes (Jager, et al., *Proc. Natl. Acad. Sci. USA*, 97(22):12198-12203 (2000)) or recombinant NY-ESO-1 protein (Davis, et al., *Proc. Natl. Acad. Sci. USA*, 101(29):10697-10702 (2004)). CD4+ T-cells play a critical role in generating and maintaining antigen specific cellular immune responses such as $CD8^+$ T cells also referred as Cytotoxic T lymphocytes (CTL's) and humoral immune responses such as antibodies. The identification and characterization of additional NY-ESO-1 peptide epitopes presented by MHC class II molecules which may be recognized by naturally induced or vaccine induced $CD4^+$ T cells remains vital for the design, development and evaluation of cancer vaccines utilizing the NY-ESO-1 antigen.

In the disclosure which follows $CD4^+$ T-cells form 3 cancer patients with NY-ESO-1 expressing tumors were stimulated with synthetic overlapping 18 mer peptides spanning the entire sequence of NY-ESO-1. Two novel peptide epitopes for NY-ESO-1 were identified that were recognized by $CD4^+$ T-cells from the 3 patients. Antigen specific $CD4^+$ T-cell clones were generated by repetitive stimulation with the novel peptide epitopes, NY-ESO-1 p49-66 and p55-72. Further experiments showed that the NY-ESO-1 p49-80-region contains at least two different $CD4^+$ T-cell epitopes. Partially histocompatible EBV-B-cell lines and MHC class II specific blocking antibodies, were used to determine that these epitopes were presented in the context of the MHC class II molecule HLA-DQ B1 03011(DQ7). Natural processing and presentation of these epitopes was indicated by NY-ESO-1 specific $CD4^+$ T cell recognition of an EBV-B-cell line expressing NY-ESO-1 and by T cell recognition of dendritic cells (DC's) exogenously loaded with NY-ESO-1 protein or infected with recombinant adenovirus-NY-ESO-1 (Ad-ESO) construct. Detectable IFN-γ and TNF-α cytokine production by the $CD4^+$ T cells and lack of IL-4 secretion indicated that the T-cell clones belonged to the Th1 subtype, the subset of T cells that play a key role in the induction of specific $CD8^+$ T-cell immunity. These new MHC (HLA) class II restricted NY-ESO-1 epitopes represent important tools to monitor spontaneous as well as peptide, protein or viral vector vaccine-induced immune responses in patients with NY-ESO-1 positive tumors or as a component of an NY-ESO-1 peptide cancer vaccine.

BRIEF DESCRIPTION OF THE FIGURES

FIG. 2 presents data relating to peptide titration assays using overlapping NY-ESO-1 peptides.

FIG. 5A depicts data obtained from dendritic cells that had been used as antigen presenting cells in ELISPOT assays while

EXAMPLE 1

Figure 1:
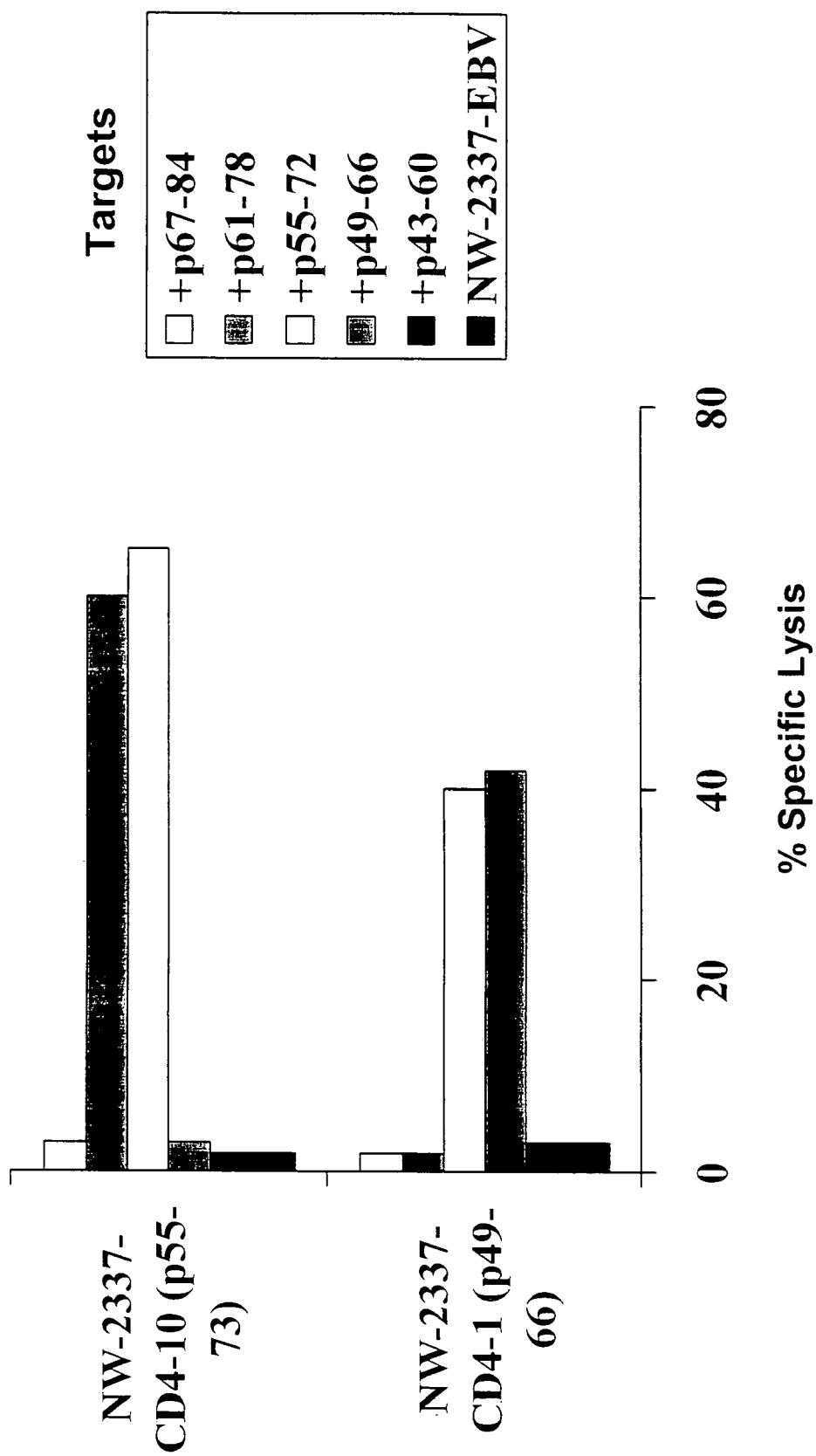
FIG. 1 presents data for $^{51}$Cr release for certain $CD4^+$ T cell clones when contacted with NY-ESO-1 peptides.

Peripheral blood mono-nuclear cells ("PBMCs") were separated from heparinized blood via Ficoll density gradient separation, using standard, art recognized techniques. Once this was done, the $CD4^+$ and $CD8^+$ T cells were separated from each other using magnetic cell sorting techniques which are well known to the art, producing $CD4^+$, $CD8^+$, and $CD4^-/CD8^-$ cell populations.

A series of 18 mer peptides were prepared from the amino acid sequence of NY-ESO-1 as set forth in, e.g., U.S. Pat. No. 5,804,381, incorporated by reference. The peptides were designed to cover the entire sequence of NY-ESO-1, and to provide overlap. The following table shows the sequences of the peptides, with reference to the master sequence.

The peptides were then individually pulsed to antigen presenting cells ("APCs"). These were $CD4^-/CD8^-$ PBMCs taken from the same subjects who had provided the $CD4^+$ and $CD8^+$ cells. These APCs were irradiated with 3000 rads, and then pulsed with one of the peptides, at a concentration of 10 μg/ml, for 1 hour, in serum free medium. These APCs were then washed, and added to the $CD4^+$ cells. In the pulsing experiments, the peptides were solubilized in DMSO (100%) and then diluted with PBS to a final concentration of 10% DMSO. The $CD4^+$ cells had been cultured in a medium of L-arginine (242 mg/l), L-asparagene (50 mg/l), L-glutamine (300 mg/l), penicillin (10 IU/ml), streptomycin (100 μg/ml), 1% non-essential amino acids, 10% HS, and 10 ng/ml of recombinant human IL-2.

The $CD4^+$ T cells were restimulated weekly with 1 μg/ml of the peptide being used. On day 12, each $CD4^+$ culture was assayed for NY-ESO-1 peptide recognition, using the ELISPOT assay of Iager, et al., *Proc. Natl. Acad. Sci. USA*, 97(9):4760-4765 (2000), incorporated by reference. To elaborate on this procedure, flat-bottomed, 96-well nitrocellulose plates were coated with 5 μg/ml of anti-interferon-gamma antibody and incubated overnight at 4° C. After washing with PBS, plates were blocked with 10% human serum (HS) for 1 hour at 37° C. Depending on the effector:target ratio used, various numbers of presensitized $CD4^+$ T-cells were added to each well along with $5 \times 10^4$ autologous peptide pulsed EBV transfected B cells ("EBV-B cells") serving as target cells and incubated for 16 hours at 37° C. in TCM without IL-2. Plates were then washed extensively (6 times with a solution of 0.05% Tween 20/PBS), and biotinylated anti-interferon-gamma detection antibody was added at a concentration of 0.5 μg/ml. After incubation for 2 h at 37° C., plates were washed and incubated with ABC-AP Vectastain for 1 hour. Plates were washed again and developed with substrate (BCIP/NPT) until blue spots were visible. The number of blue spots/well represented the proportion of NY-ESO-1 specific $CD4^+$ T-cells/well was finally counted under the microscope.

The EBV-B-cells were generated from each patients' PBMC following standard methods and maintained in RPMI 1640 medium supplemented with 10 mM Hepes buffer, L-arginine (242 mg/l), L-asparagine (50mg/l), L-glutamine (300 mg/l), penicillin (10 IU/ml), streptomycin (100 μg/ml), 1% non-essential amino acids, and 10% FCS. All EBV-B- cells had been analyzed in RT-PCR for NY-ESO-1 mRNA expression and were negative except for the MZ-1257 EBV-B-cell line. PBMC's or EBV-B-cells were molecularly typed for HLA expression using standard procedures.

Six NY-ESO-1 18mer peptides were found to stimulate an INF-γ effector response from stimulated CD4+ T cells from the patients tested as indicated in the Table, which follows.

TABLE

| Peptide | Patient T cells | | |
|---|---|---|---|
| | 1 | 2 | 3 |
| p1-18 | − | − | − |
| p7-24 | − | − | − |
| P13-30 | − | − | − |
| P19-36 | − | − | − |
| P25-42 | − | − | − |
| P31-48 | − | − | − |
| P37-54 | − | − | − |
| P43-60 | − | + | − |
| P49-66 | + | + | + |
| P55-72 | + | + | + |
| P61-78 | + | + | + |
| P67-84 | − | − | − |
| P73-90 | − | − | − |
| P79-96 | − | − | − |
| p85-102 | − | − | − |
| p91-108 | − | − | − |
| p97-114 | − | + | − |
| p103-120 | − | + | − |
| p109-126 | − | − | − |
| p115-132 | − | − | − |
| p121-138 | − | − | − |
| p127-144 | − | − | − |
| p133-150 | − | − | − |
| p139-156 | − | − | − |
| p145-162 | − | − | − |
| p151-168 | − | − | − |
| p157-174 | − | − | − |
| p163-180 | − | − | − |

− indicates <50 spots
+ indicates >50 spots (all + scores indicated were >100 spots)

It will be seen that recognition of NY-ESO-1 peptides p 43-60, p97-114 and p103-120 was observed with CD4$^{30}$ T cells from one patient, and NY-ESO-1 peptides p49-66, p55-72 and p61-78 stimulated CD4+ T-cells in all three patients.

EXAMPLE 2

Peptides p49-66 and p55-72 were then used to generate peptide specific CD4+ T-cell lines and clones from patient NW2337 using standard limiting dilution methods (Jager, et al., *J. Exp. Med.*, 191(4):625-630 (2000)). Briefly, CD4+ T-cells from polyclonal peptide stimulation cultures were cloned by limiting dilution at 1 cell/well in 96 U-bottom plates by using irradiated (10.000 rad) peptide-pulsed autologous EBV-B-cells as APCs and feeder cells simultaneously in TCM at 30,000 cells/well. After 2 weeks, with one restimulation as described supra, on day 7, aliquots of proliferating clones were tested for NY-ESO-1 specific reactivity in ELISPOT assays, also as described supra, NY-ESO-1 peptide specific CD4+ clones were restimulated weekly as described.

A total of 27 CD4+ T-cell clones were generated by stimulation with p49-66 and a total of 53 CD4+ T-cell clones were generated by stimulation with p55-72. All clones obtained in separate presensitization cultures had specificity for the stimulating peptide when tested in ELISPOT assay.

EXAMPLE 3

In these experiments, exemplary clones NY-ESO-1 p49-66 specific CD4+ T cell clone NW2337-CD4-1 and NY-ESO-1 p55-72 specific CD4+ T cell clone NW2337-CD4-10 were characterized in $^{51}$Chromium ($^{51}$Cr) release assays using peptides overlapping the sequence of each stimulation peptide. Standard $^{51}$Cr release assay methods were used. Briefly, autologous EBV B cell target cells were labeled with 100 μCi Na$_2$$^{51}$CrO$_4$ for 2 hours, and pulsed with 18 mer or 20 mer NY-ESO-1 peptides (10 μg/ml) for 1 hour. Then, 1×10$^3$ target cells/well were incubated in 96 V- bottom microwell plates with effector cells at different E/T ratios for 4 h at 37° C. $^{51}$Cr release was measured in the supernatant and the specific cytotoxicity was calculated using the standard methods. Polyclonal T-cell populations were preincubated with unlabeled K562 cells as competitors at a concentration of 40:1 in order to block non-specific effector reactions.

Representative $^{51}$Cr.release assay data for CD4+ T cell clones NW2337-CD4-1 and NW2337-CD4-10, is provided in FIG. 1. The two clones showed different peptide recognition patterns. Clone NW2337-CD4-1, generated by in vitro stimulation with NY-ESO-1 p49-66 recognized this peptide but also crossreacted with NY-ESO-1 p55-72 (FIG. 1). Clone NW2337-CD4-10 generated by in vitro stimulation with NY-ESO-1 p55-72, recognized this peptide, but did not crossreact with the NY-ESO-1 p49-66 peptide. Instead, this clone crossreacted with the overlapping NY-ESO-1 p61-78 peptide (FIG. 1). This indicates that the two clone are recognizing overlapping but distinct peptide epitopes.

EXAMPLE 4

Figure 3:
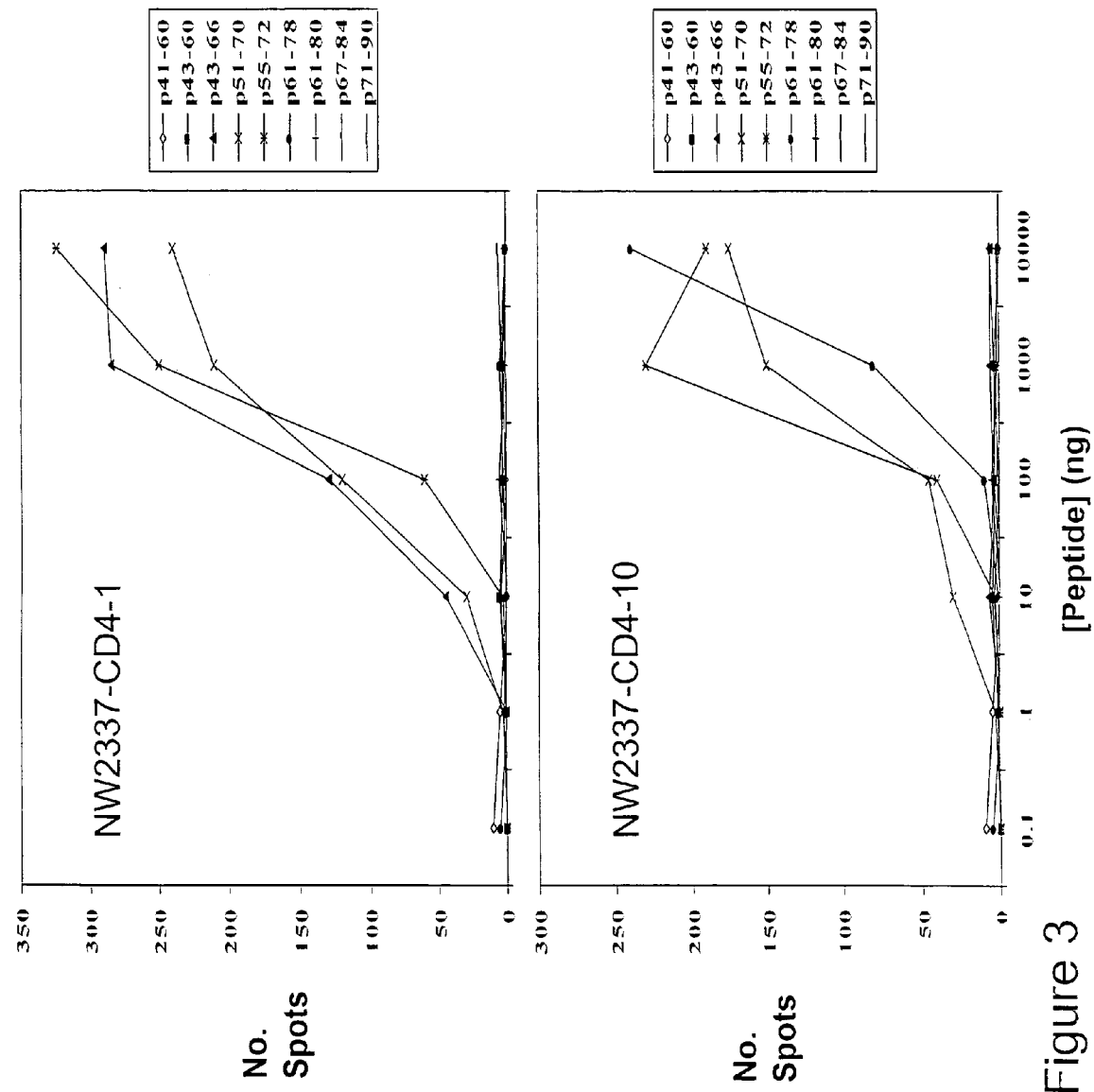
FIG. 3 depicts results of ELISPOT assays using these peptides.

To further identify the exact epitope required for CD4+ T cell recognition by these two CD4+ T cell clones, a peptide titration assay was performed using overlapping NY-ESO-1 peptides (FIG. 2) at concentrations between 10 μM and 0.1 nM, pulsed onto autologous EBV-B-cells and tested in ELISPOT assays (FIG. 3). Clone NW2337-CD4-1 recognized three overlapping peptides, i.e., p49-66, p51-70 and p55-72 indicating that the MHC class II restricted CD4+ T cell epitope is located within the 49-72 amino acid region of NY-ESO-1 (FIG. 2 & FIG. 3, upper panel). The second MHC class II restricted CD4+ T cell epitope recognized by clone NW2337-CD4-10 is located within the 55-80 amino acid region of NY-ESO-1 since this clone is able to recognize peptides p55-72, p61-78 and 61-80 (FIG. 2 & FIG. 3, lower panel).

Typically, peptides binding to MHC class II molecules are predicted to be 12-25 amino acids in length, although due to the open structure of the peptide binding groove of MHC class II molecules, restrictions on the length of peptides able to bind class II molecules is much stringent than for MHC class I molecules. The specificity of peptide recognition exhibited by the two clones suggest the existence of two distinct MHC class II restricted, CD4+ T cell peptide epitopes within the amino acids 49-80 region of the NY-ESO-1 antigen.

Clone NW2337-CD4-1 was originally stimulated with peptide NY-ESO-1 p49-66 recognized three overlapping peptides. The core peptide epitope NY-ESO-1 p55-66, recognized by this T cell clone is represented by the overlapping portion of the three recognized peptides (FIG. 2).

Clone NW2337-CD4-10 was originally stimulated with peptide NY-ESO-1 p55-72 recognized three overlapping peptides. The core peptide epitope NY-ESO-1 p61-72, recognized by this T cell clone is represented by the overlapping portion of the three recognized peptides (FIG. 2).

EXAMPLE 5

In order to determine the HLA molecule to which the novel NY-ESO-1 peptides described above bind, the NW2337 CD4+ T-cell clones NW2337-CD4-1 and NW2337-CD4-10, were tested in ELISPOT assays using a range of peptide pulsed allogeneic EBV-B-cells with known HLA class II types as stimulator cells as indicated in the following Table. The EBV-B-cell lines were HLA typed using standard methods as described above.

TABLE 2

| EBV-B cell | DR | DR | DP | DP | DQ | DQ |
| --- | --- | --- | --- | --- | --- | --- |
| NW-1672 | B1 07 | B1 13 | B1 02012 | B1 0401 | B1 0201 | B1 06041 |
| NW-2082 | B1 04 | B1 15 | B1 0401 | | B1 0201 | B1 0602 |
| NW-29 | B1 15 | B1 07 | | | | |
| NW-2078 | B1 12 | B1 16 | B1 02012 | B102013 | B1 03011 | B1 0602 |
| NW-2081 | B1 03 | B1 13 | B1 0401 | B1 5101 | B1 0201 | B1 03011 |
| NW-1789 | B1 07 | B1 15 | B1 0301 | B1 1301 | B1 03032 | B1 0602 |
| NW-2395 | B1 0104 | B1 15 | B1 0401 | B1 0402 | B1 03011 | B1 0602 |
| NW-2234 | B1 12 | | B1 0401 | B1 0402 | B1 03011 | B1 03 |
| NW-2231 | | | B1 0401 | | B1 0201 | B1 03 |
| NW-961 | B1 01 | B1 15 | B1 0401 | B1 0402 | B1 05 | B1 06 |
| NW-2281 | B1 03011 | B1 14 | B1 0401 | B1 3301 | B1 0201 | B1 0531 |
| NW-2337 | B1 11 | B1 13 | B1 0301 | B1 0401 | B1 03011 | B1 0402 |
| NW-1100 | B1 11 | | B1 02 | B1 04 | B1 03011 | |
| MZ-1257 | B1 11 | B1 15 | B1 0401 | B1 0402 | B1 03011 | B1 0602 |

Figure 4A:
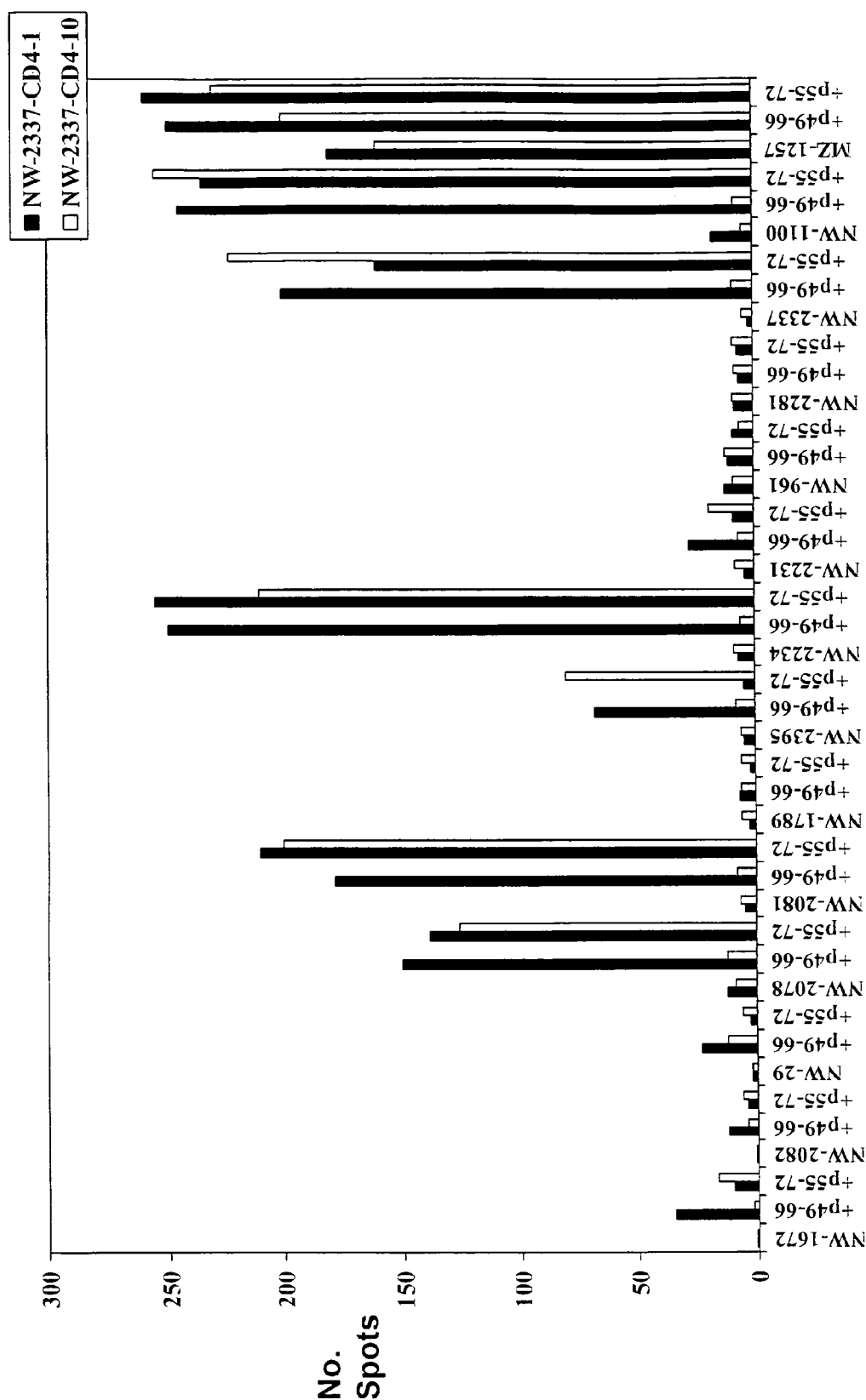
FIG. 4A sets forth results of additional ELISPOT assays, while FIG. 4B sets forth results of antibody blocking assays.

The results of this series of ELISPOT assays are summarized in FIG. 4A. The NW2337-CD4-1 clone recognized allogenic peptide pulsed EBV-B cells from patients NW-2078, NW-2081, NW-2395, NW-2234, NW-2337, NW-1100 and MZ-1257. The allogenic EBV-B cells were recognized by the T cells when pulsed exogenously with either the NY-ESO-1 p49-66 or p55-72 as observed with autologous EBV-B cells described above. Recognition by the NW2337-CD4-1 T cells of MZ-1257 EBV-B cells was observed with and without pulsing of exogenous NY-ESO-1 peptide since this B cell line expressed NY-ESO-1 endogenously. By comparing the HLA expression profiles the EBV-B-cell lines it was determined that the only shared MHC class II allele expressed by all the EBV-B-cell lines recognized by the NW2337-CD4-1 T cells was HLA-DQB1 03011. None of the EBV-B-cells lines that were not recognized by the T cells expressed this MHC allele. Similarly, the NW2337-CD4-10 T cells recognized only HLA-DQB1 03011 expressing allogenic EBV-B cell lines, those from patients NW-2078, NW-2081, NW-2395, NW-2234, NW-2337 and NW-1100 when pulsed exogenously with NY-ESO-1 p55-72 peptide. Again the NY-ESO-1 positive MZ-1257 EBV-B-cell line was recognized with or without exogenous peptide. These results indicate that the NW2337 CD4+ T-cell clones NW2337-CD4-1 and NW2337-CD4-10 each recognize the respective novel NY-ESO-1 peptide epitopes when they bind to form a complex with the human MHC class II allele HLA-DQB1 03011.

Figure 4B:
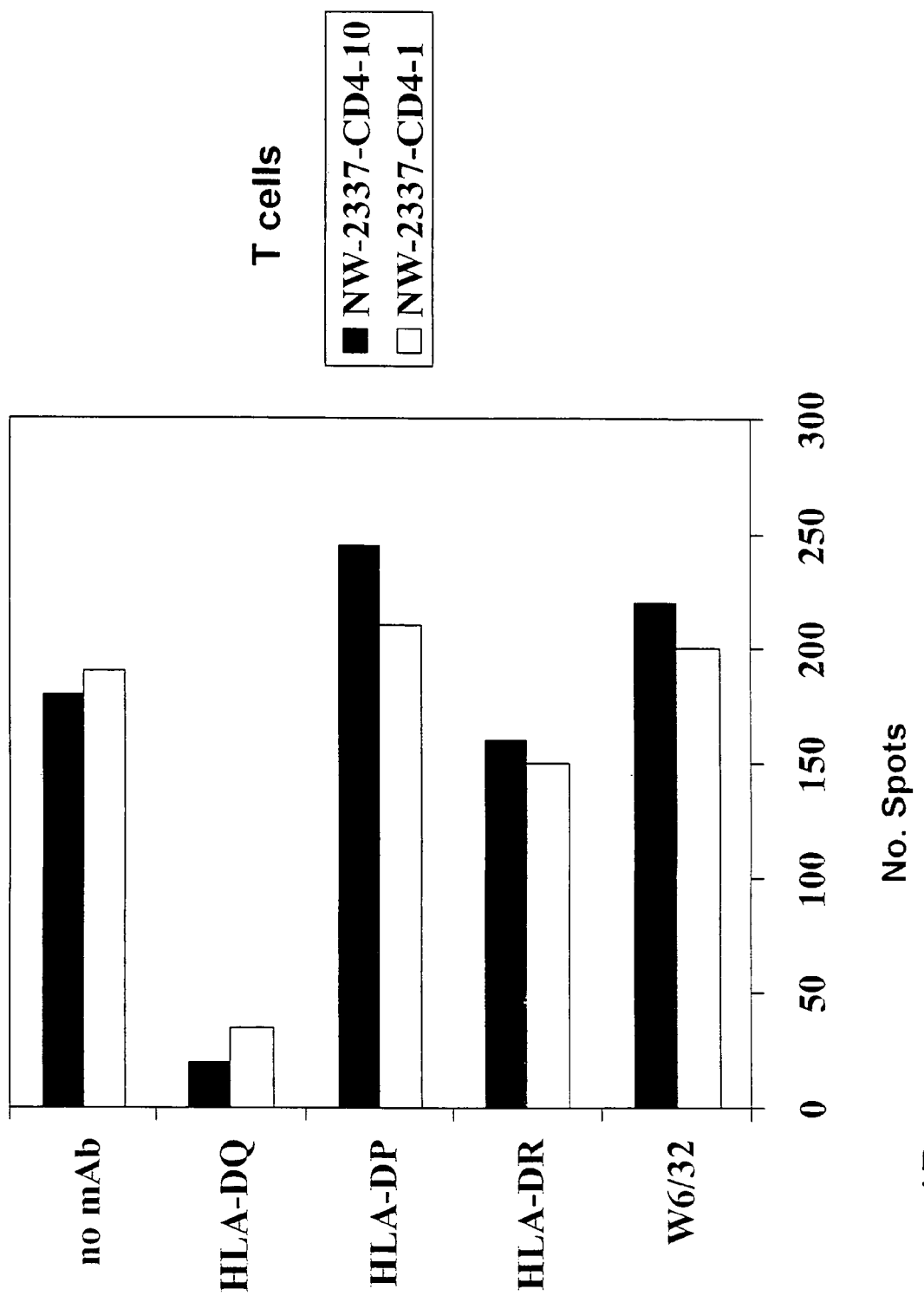

To confirm these results, an antibody blocking assay was performed using the NY-ESO-1 and HLA-DQB1 03011 expressing MZ1257 EBV-B-cell line. This cell line was used as the APC's in ELISPOT assays where these stimulator cells were preincubated with monoclonal antibodies (mAbs) specific for HLA class I (W6/32), HLA-DP, HLA-DR (L243) and HLA-DQ (Biomol 3H222). As indicated in FIG. 4B, recognition of MZ1237 EBV-B-cells by NW2337-CD4-1 and NW2337-CD4-10 T cells was reduced compared to MZ1237 EBV-B-cells with no antibody, when the stimulator cells were incubated with the anti-DQ antibody. Stimulator cells incubated with antibodies against MHC class II DR and DP retained the capacity to stimulate recognition by both T cell clones.

EXAMPLE 6

Figure 5A:
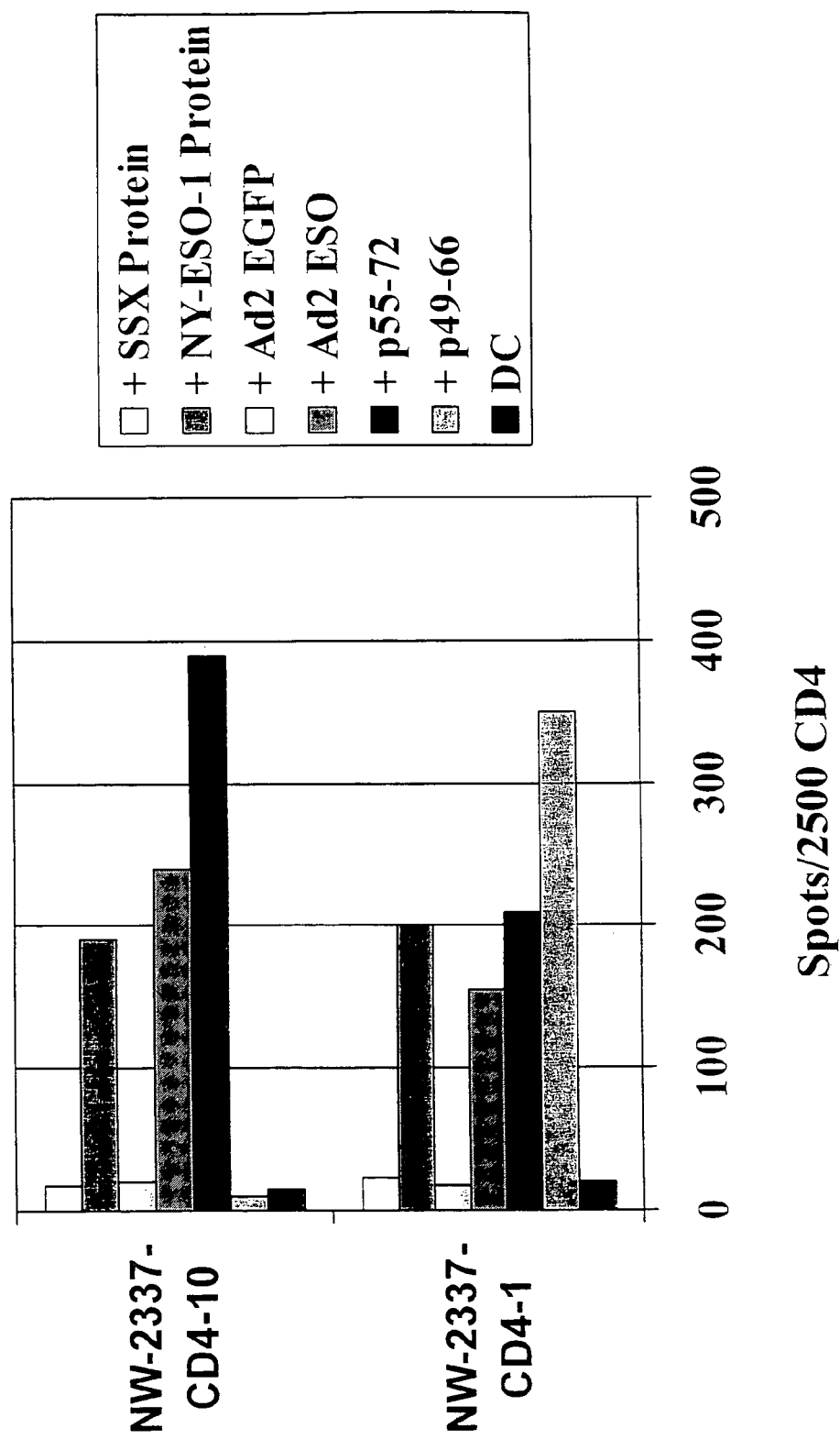

To formally demonstrate that the NW2337 CD4+ T-cell clones generated by repetitive NY-ESO-1 p49-66 or p55-72 peptide stimulation, were able to recognize naturally processed NY-ESO-1 epitopes in the context of HLA-DQB1 03011 additional ELISPOT assays were performed using allogenic HLA-DQ matched dendritic cells (DC's). To prepare the DC's, PBMC were incubated in T30 tissue culture flasks for 2 h at 37° C. Nonadherent cells were removed, and adherent cells were cultured with GM-CSF 1000 U/ml (Leukomax, Sandoz, Nürnberg, Germany), and IL-4 1000 U/ml (Pharma Biotechnologie Hannover, Germany) for 5 days in X-Vivo15 medium (Bio Whittaker, Walkersville, Md., USA) 2 ml/well. DC's were treated on day 6 of in vitro culture with IL-4 1000 U/ml, IL-6 1000 U/ml, 1L-1β 10 ng/ml, TNFalpha 10 ng/ml (IL-4, IL-6, IL-1β, TNFalpha obtained from Pharma Biotechnologie Hannover, Germany), GM-CSF 1000 U/ml, and prostaglandin 1 μg/ml (Sigma Chemical Co., St. Louis, Mo.). The DC's were infected with a recombinant adenovirus construct expressing NY-ESO-1 (Ad2/ESO) at 1000 infection units/cells, or pulsed with recombinant NY-ESO-1 protein (10 ug/ml) or pulsed with peptides at 10 μg/ml and cultured for 24 hours. Treated DC were then washed twice and used as APC in ELISPOT assay. DC's treated with Ad2/ESO or recombinant NY-ESO-1 were used as APC presenting naturally processed NY-ESO-1 peptides. NW-2337-CD4-1 and NW-2337-CD4-10 T cells recognized these DC's infected with Ad2/ESO or pulsed with recombinant NY-ESO-1 protein (FIG. 5A). This confirmed that the peptides epitopes recognized by the T cells could be naturally processed and presented by APC's expressing NY-ESO-1. No T cell stimulation was observed when DCs were incubated with either a control recombinant adenovirus construct expressing an irrelevant protein EGFP (Ad2/EGFP), or when exogenously pulsed with a control recombinant SSX protein.

Figure 5B:
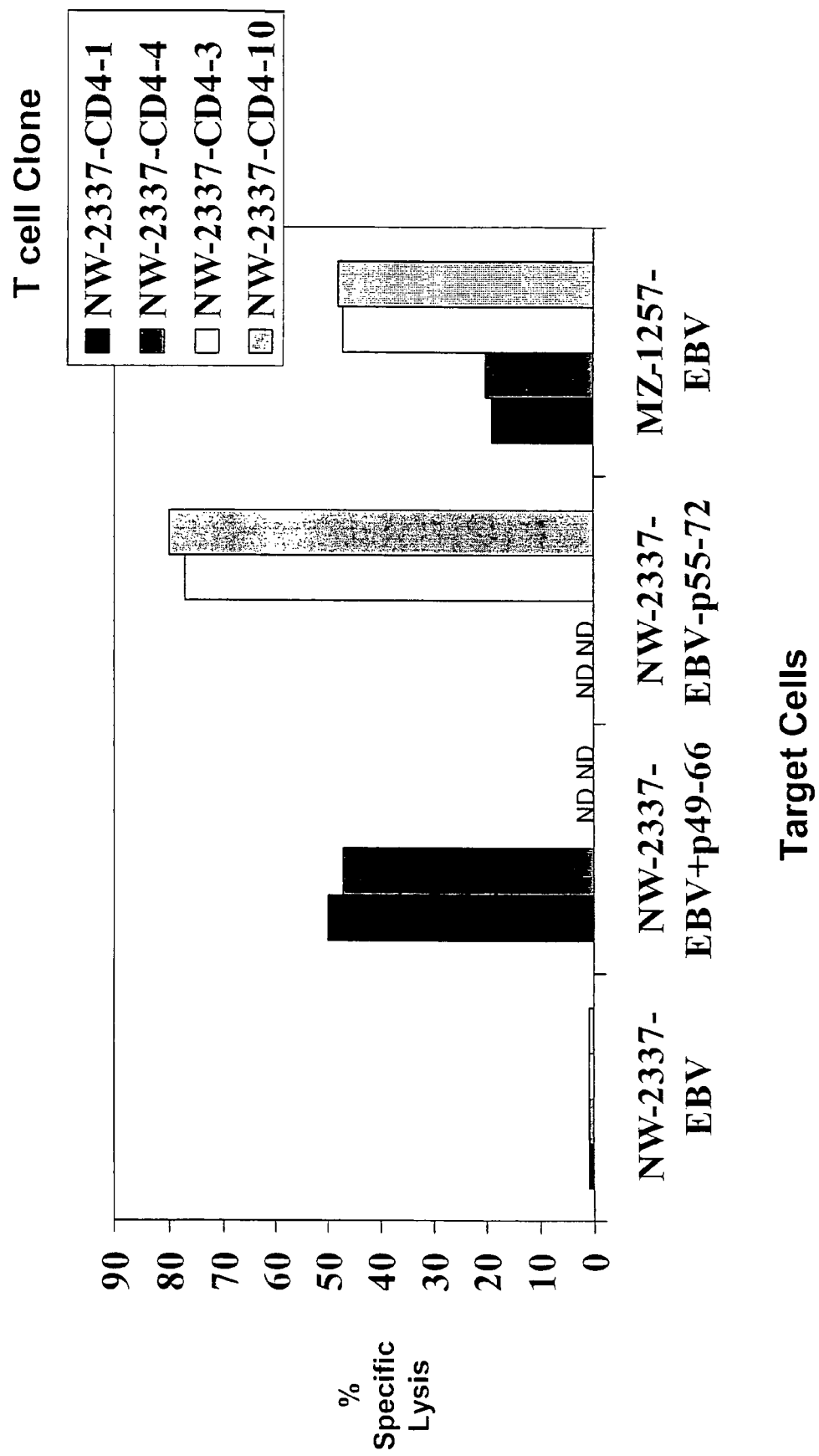
FIG. 5B presents the results of $CD4^+$ T cell assays.

These results were further confirmed by using the NY-ESO-1/HLA-DQB1 03011 expressing B-cell line MZ-1257-EBV as a target in $^{51}$Cr release assays. CD4+ T-cell clones NW-2337-CD4-1 and -4 specific for NY-ESO-1 p49-66 efficiently lysed the peptide pulsed (p49-66) autologous NW-2337-EBV B-cell lines and the unpulsed MZ-1257-EBV B-cell line (FIG. 5B). Whereas, CD4+ T-cell clones NW-2337-CD4-3 and -10 specific for NY-ESO-1 p55-72 efficiently lysed the peptide pulsed (p55-72) autologous NW-2337-EBV B-cell lines and the unpulsed MZ-1257-EBV B-cell line. These experiments confirmed recognition of naturally presented NY-ESO-1 epitopes by the CD4+ T-cell clones.

All ELISPOT assay described, supra were designed to detect IFN-γ secretion by the T cell clones following specific antigen stimulation. To determine the phenotype of the NY-ESO-1 specific CD4+ T cell clones from patient NW2337, additional ELISPOT assays were designed to detect additional cytokines.

The NW2337 CD4+ T cells were stimulated with either NY-ESO-1 p49-66 and p55-72 peptides and T cells secretion of IFNγ, TNFα, IL4 and IL10 measured by ELISPOT assay. The results of these ELISPOT assays indicated that the stimulated T cell clones produced IFN-γ and TNF-α. IL4 and IL10 was not secreted by any of the NY-ESO-1 specific CD4+ T-cell clones tested following stimulation with NY-ESO-1 p49-66 and p55-72 peptides. These results indicated that the NY-ESO-1 specific CD4 T cell clones were of the Th1 phenotype.

EXAMPLE 7

Previous studies demonstrated that peptides from NY-ESO-1 may be able recognized by both CD4+ and CD8+ antigen-specific T-cells. To examine the possibility that one of the novel MHC class II epitopes described in this study may also represent an MHC class I binding peptide epitope, CD8+ T-cells from the patients described above, were presensitized with autologous CD4−/CD8− PBMC infected with the recombinant adenovirus Ad2/ESO. Responder T-cells were tested in ELISPOT assays for recognition of autologous APC's pulsed with the 28 overlapping 18 mer peptides described in Table 2. Recognition of NY-ESO-1 peptide p55-72 was observed with CD8+ T-cells derived from patient NW1231, NW1454 and NW2427. MHC class I typing of these patients revealed that HLA-A3 was the only shared HLA class I allele indicating that the NY-ESO-1 p55-72 peptide was presented by HLA-A3 molecules. The HLA-A3 restricted recognition of p55-72 was further demonstrated by NW1454 CD8+ T-cell recognition of T2-A3 and HLA-A3 expressing NW115 EBV-B-cell target cells when pulsed with NY-ESO-1 p55-72 peptide.

The invention claimed is:

1. An immunogenic peptide composition comprising at least one peptide which consists of an amino acid sequence sleeted from the group consisting of:
amino acids 1-18 of SEQ ID NO 1;
amino acids 7-24 of SEQ ID NO: 1;
amino acids 13-30 of SEQ ID NO: 1;
amino acids 19-36 Of SEQ ID NO: 1;
amino acids 25-42 of SEQ ID NO: 1;
amino acids 31-48 of SEQ ID NO: 1;
amino acids 37-54 of SEQ ID NO: 1;
amino acids 43-60 of SEQ ID NO: 1;
amino acids 49-66 of SEQ ID NO: 1;
amino acids 55-72 of SEQ ID NO: 1;
amino acids 61-78 of SEQ ID NO: 1;
amino acids 73-90 of SEQ ID NO: 1;
amino acids 79-96 of SEQ ID NO: 1;
amino acids 97-114 of SEQ ID NO: 1;
amino acids 133-150 of SEQ ID NO: 1;
amino acids 145-162 of SEQ ID NO: 1;
amino acids 151-168 of SEQ ID NO: 1; and
amino acids 163-180 of SEQ ID NO: 1.

2. The immunogenic peptide composition of claim 1, wherein said pharmaceutically acceptable cater is an adjuvant.

3. The immunogenic peptide composition of claim 2, wherein said adjuvant is a saponin, a cytokine, or immune-modulator.

4. The immunogenic peptide composition of claim 1, wherein said composition comprises a plurality of peptides each of which complexes with a specific MHC molecule.

5. An isolated polypeptide consisting of an amino acid sequence selected from the group consisting of:
amino acids 1-18 of SEQ ID NO: 1;
amino acids 7-24 of SEQ ID NO; 1;
amino acids 13-30 of SEQ ID NO: 1;
amino acids 19-36 of SEQ ID NO: 1;
amino acids 25-42 of SEQ ID NO: 1;
amino acids 31-48 of SEQ ID NO: 1;
amino acids 37-54 of SEQ ID NO: 1;
amino acids 43-60 of SEQ ID NO: 1;
amino acids 49-66 of SEQ ID NO: 1;
amino acids 55-72 of SEQ ID NO: 1;
amino acids 61-78 of SEQ ID NO: 1;
amino acids 73-90 of SEQ ID NO: 1;
amino acids 79-96 of SEQ ID NO: 1;
amino acids 97-114 of SEQ ID NO 1;
amino acids 133-150 of SEQ ID NO: 1;
amino acids 145-162 of SEQ ID NO: 1;
amino acids 151-168 of SEQ ID NO: 1; and
amino acids 163-180 of SEQ ID NO: 1.

6. The isolated polypeptide of claim 5, wherein the polypeptide binds to an MHC molecule to form an MHC epitope complex.

7. The polypeptide of claim 6, wherein the MHC epitope complex is recognized by a T cell.

8. The isolated peptide of claim 5, consisting of an amino acid sequence selected from the group consisting of amino acids 43-60 of SEQ ID NO: 1, amino acids 97-114 of SEQ ID NO: 1, amino acids 49-66 of SEQ ID NO: 1, amino acids 55-72 of SEQ ID NO: 1, and amino acids 61-78 of SEQ ID NO: 1.

9. A method for treating a subject afflicted with an NY-ESO-1 expressing cancer, comprising administering said subject a therapeutically effective amount of the peptide of claim 8, in an amount sufficient to alleviate said cancer.

10. The method of claim 9, comprising administering said peptide in combination with an adjuvant.

11. A composition of matter useful in treating a cancerous condition, comprising the peptide of claim 8, and a pharmaceutically acceptable carrier.

* * * * *

UNITED STATES PATENT AND TRADEMARK OFFICE
CERTIFICATE OF CORRECTION

PATENT NO. : 7,632,506 B2
APPLICATION NO. : 11/219610
DATED : December 15, 2009
INVENTOR(S) : Elke Jager It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 725 days.

Signed and Sealed this

Second Day of November, 2010

David J. Kappos
*Director of the United States Patent and Trademark Office*